United States Patent [19]

Jones

[11] Patent Number: 4,790,260

[45] Date of Patent: Dec. 13, 1988

[54] INSECT ACTUATED NOVELTY DEVICE

[76] Inventor: Thomas K. Jones, 737 Popular St., Langhorne, Pa. 19047

[21] Appl. No.: 825,716

[22] Filed: Feb. 3, 1986

[51] Int. Cl.$^4$ .............................................. A01K 1/00
[52] U.S. Cl. ......................................... 119/1; 119/15; 119/17; 119/29; D30/160
[58] Field of Search ....................... 119/15, 17, 18, 23, 119/29, 32, 1; D30/1, 41, 42

[56] References Cited

U.S. PATENT DOCUMENTS

| | | |
|---|---|---|
| Re. 18,273 | 12/1931 | Freer . |
| 80,561 | 8/1868 | Osborn .................................. 119/17 |
| D. 236,513 | 8/1975 | Palmer .................................. D30/42 |
| D. 239,948 | 5/1976 | Perkins ................................. D30/1 |
| D. 270,297 | 8/1983 | Lovitt .................................. D30/1 |
| 511,272 | 12/1893 | Hughes . |
| 583,661 | 6/1897 | Smith . |
| 1,632,380 | 6/1927 | Marcus . |
| 1,794,951 | 3/1931 | Freer . |
| 2,640,460 | 6/1953 | Siegel . |
| 2,778,333 | 4/1955 | Babros et al. . |
| 3,173,398 | 3/1965 | Raymond .............................. 119/29 |
| 3,653,357 | 4/1972 | Sheidlower et al. ............. 119/15 X |
| 4,227,487 | 10/1980 | Davis .................................... 119/29 |
| 4,480,587 | 11/1984 | Sedlacek .......................... 119/17 X |
| 4,498,421 | 2/1985 | Lovitt . |
| 4,577,589 | 3/1986 | Voss et al. ........................... 119/17 |

FOREIGN PATENT DOCUMENTS 1415574  11/1975  United Kingdom .

Primary Examiner—David A. Scherbel
Assistant Examiner—Richard E. Chilcot, Jr.
Attorney, Agent, or Firm—Caesar, Rivise, Bernstein, Cohen & Pokotilow, Ltd.

[57] ABSTRACT

An amusement device adapted to receive and contain therein one or more insects or small bugs. The device includes a rectangular box-shaped container made of transparent material. The container is open on one side thereof and a cover is removably fitted over and extends into the opening in order to close the opening. A wheel assembly is vertically mounted within the container, and the wheel assembly is rotatable about a horizontal axis. Also provided within the container is a stepless ramp which extends upwards at an angle from the bottom of the container over the wheel assembly.

8 Claims, 1 Drawing Sheet

INSECT ACTUATED NOVELTY DEVICE

BACKGROUND OF THE INVENTION

The present invention relates to an insect cage, and in particular, the invention relates to a transparent cage or container for retaining an insect and which has a ramp for the insect to climb into a rotatable wheel.

Numerous types of cages and containers for animals and birds are known in the prior art and many of these cages have wheels or exercise devices for the creatures contained therein. Often, the devices smiply consist of a cage containing a wheel, or in some cases a disk, which is mounted for rotation. Most usually, the animal enters the wheel and causes the wheel to rotate by walking around the interior surface of the wheel.

Specific types of cages and exercise devices for animals and birds are shown in U.S. Pat. Nos. 511,272 to Hughes, 1,632,380 to Marcus, 2,640,460 to Siegel, 1,794,951 and Re. 18,273 to Freer, and 4,498,421 to Lovitt. All of these patents show different types of exercise devices for animals, rodents or birds, wherein a rotatable wheel is provided.

In U.S. Pat. No. 511,272 to Hughes and British Patent No. 1,415,574 to Willinger, et al., the patents disclose exercise devices employing a rotatable device upon which an animal or rodent can exercise, and in addition a set of steps is provided so that the animal or rodent can mount the rotatable device. In the Willinger, et al. device the rotatable member is a wheel mounted for rotation about a horizontal axis, and in the Hughes device, the rotatable member is a planar disk mounted for rotation about a generally veritically oriented, but slightly inclined, axis.

The prior cages and exercise devices allow the animal, bird or rodent to generally exercise or move about inside the wheel device which is provided. While the prior devices are provided for use by animals, birds and rodents, a need further exists for some type of device for use with insects and extremely small creatures. Furthermore, in providing a device of the size compatible with an insect, it is also desirable to provide an apparatus which, unlike the prior art devices, is adapted so that the insect can easily mount the outside of a vertical exercise wheel in addition to moving about within the wheel.

OBJECTS OF THE INVENTION

With the above background in mind, it is a primary object of the present invention to provide a transparent container for insects with a rotatable exercise wheel therein.

It is a further object of the invention to provide a container for an insect or a pluarlity of insects which has an inclined stepless ramp within the container that extends above the circumference of a rotatable exercise wheel so that the insects can ascend the ramp and mount the outside surface of the wheel.

A still further object of the invention is to provide a transparent container so that the movement of the insects there-inside can be easily viewed.

Yet a further object of the invention is to provide a container for housing insects which has a top that is easily fitted to and removable from the container.

Another object of the invention is to provide a container for housing insects which contains an exercise wheel which is easily inserted into and rotatably mounted within the container beneath an inclined ramp.

SUMMARY OF THE INVENTION

In furtherance of these objectives, an amusement device for use with insects and bugs is provided which has a container and a cover for the container. The container is in the shape of a rectangular box with an open top. The cover fits into and closes the open top. Inside the container is a vertical wheel assembly axially mounted in rotation about a horizontal axis. A stepless ramp is provided inside the container which extends upwards at an angle from the bottom of the container over the circumference of the wheel assembly.

Insects can climb into the wheel assembly or can ascend the ramp and crawl onto the outside of the wheel assembly where their weight will cause the wheel assembly to rotate.

Air hole openings are provided in the cover, and the ramp has a textured surface for improved traction.

DESCRIPTION OF THE DRAWINGS

Other objects and many of the attendant advantages of the instant invention will be readily appreciated as the same become understood by reference to the following detailed description when considered in connection with the accompanying drawing wherein.

DETAILED DESCRIPTION OF THE PREFERRED EMBODIMENT

Figure 1:
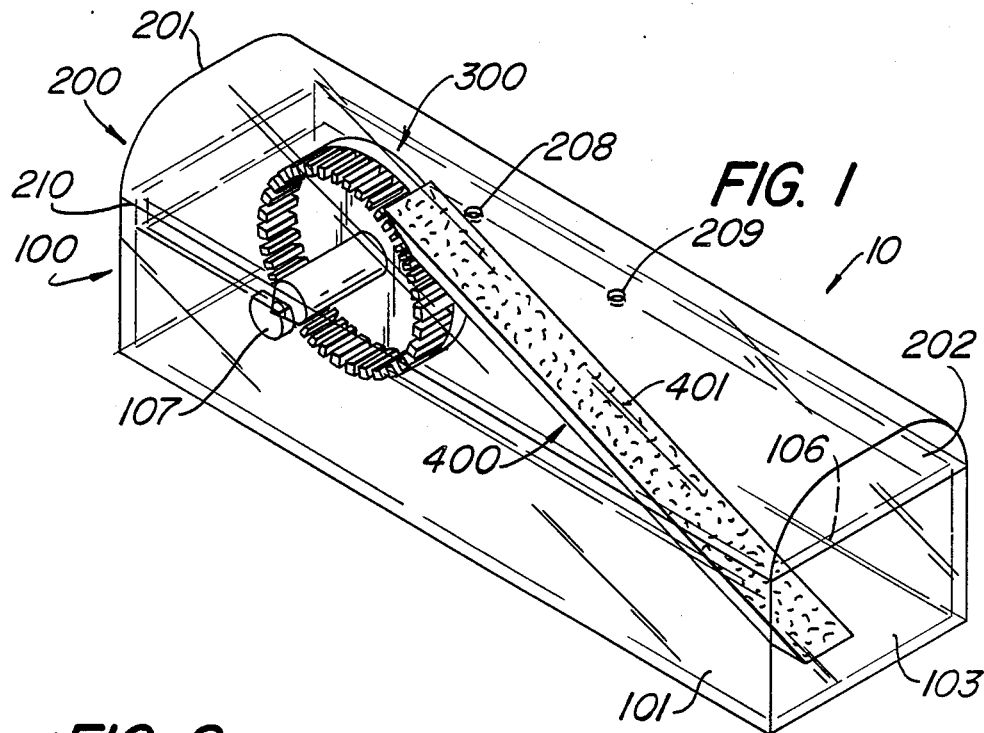
FIG. 1 is a perspective view of the insect amusement device of the present invention.

Referring now in greater detail to the various figures of the drawings wherein like reference characters refer to like parts, an insect actuated novelty device or amusement assembly of the present invention is generally shown at 10 in FIG. 1. The amusement assembly 10 comprises, generally, a container 100, a domed cover 200 which removably fits into the top of the container 100, an exercise wheel assembly 300 rotatably mounted within the container 100, and a ramp 400 secured to the bottom of the container 100 and inclined upward and over the wheel 300 within the container.

Figure 2:
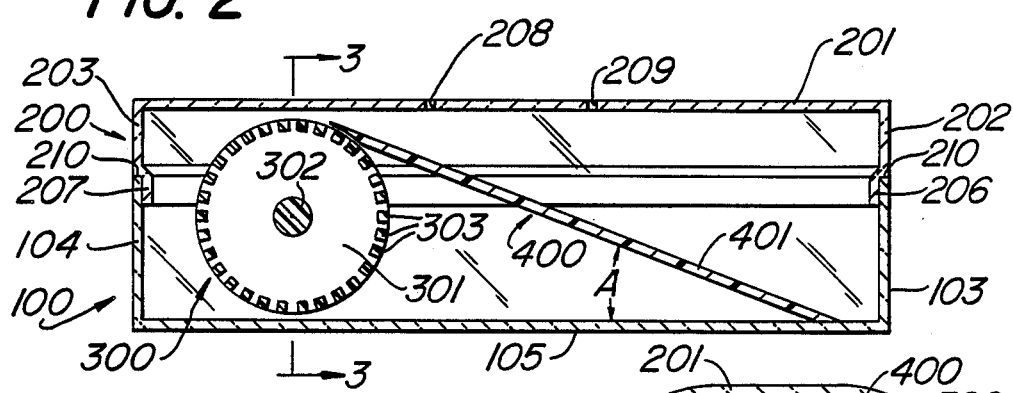
FIG. 2 is a cross-sectional view of the insect amusement device of the present invention.
Figure 3:
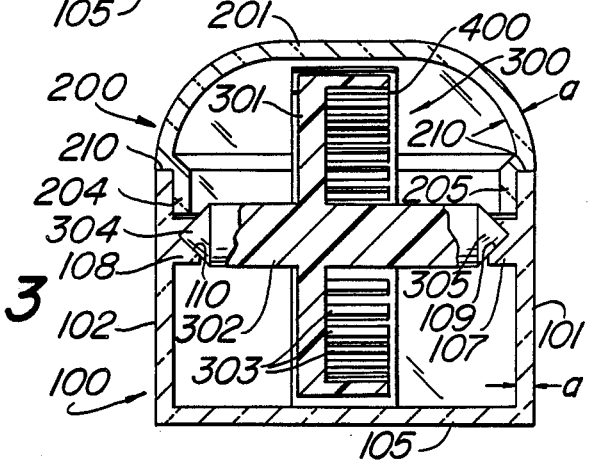
FIG. 3 is a sectional view taken along line 3—3 in FIG. 2 showing the wheel of the device in cross-section.

As shown in FIGS. 1-3, the container 100 is, preferably, rectangular and has side walls 101, 102 and end walls 103, 104. The side walls and end walls are connected to a bottom 105 to form a box-like structure. The entire top 106 of the container 100 opposite the bottom 105 is, preferably, open. It is also preferred that the container 100 be made from transparent material so that the activities of the insects therein can be easily viewed. Transparent plastic material such as "Lucite" is preferred; however, other materials such as glass and fine wire mesh are acceptable substitutes.

The cover 200 as shown in FIGS. 1-3, consists of a curved outer surface 201 and end pieces 202, 203 at each end of the curved outer surface 201. Two vertical side extensions 204, 205 (FIG. 3) are attached within and along each side of the curved outer surface 201 and extend downward therefrom, and two end extensions 206, 207 (FIG. 2) are mounted within and extend downward from the end pieces 202, 203, respectively.

As shown in FIGS. 2 and 3, the side extensions 204, 205 and the end extensions 206, 207 of the cover 200 fit inside the side walls 101, 102 and the end walls 103, 104, respectively, of the container 100. With the extensions 204-207 in position within the open top 106, the cover 200 completely closes the open top 106 of the container 100. The dimensions of the extensions 204-207 are slightly smaller than the inside dimensions of the side walls 101, 102 and the end walls 103, 104 so that the extensions 204-207 fit slideably inside the top 106 of the container 100, yet securely, frictionally engage the side walls 101, 102 and end walls 103, 104. In this manner, the cover 200 is held tightly in the open top 106 of the container by the frictional engagement between the extensions 204-207 and the walls 101-104 of the container 100. In order to present a good outward appearance, the curved outer surface 201 and the end covers 202,203 fit smoothly with the side and end walls 101-104 (FIGS. 2 and 3) so that a flush appearance is created at the junction 210 of the cover 200 and the container 100.

In the top of the cover 200 are holes 208, 209 which allow air to enter into the container when the cover is in position within the side walls of the container 100.

The exercise assembly wheel 300 of the present invention includes a circular plate 301 which is axially mounted onto an axle or spindle 302. Affixed to the circular plate 301 and extending outward from the plate substantially around the circumference thereof, are a plurality of spokes 303. These spokes are spaced from each other by a distance approximately equal to the width of each spoke and as shown in FIGS. 1 and 2, the spokes 303 are parallel to the axle or spindle 302. The axle 302 has is a cylindrical rod shape with tapered ends 304, 305, and the entire wheel assembly 300 is preferably made of plastic material.

As shown in FIGS. 1 and 2, on the inside surfaces of the side walls 101, 102 are wheel mounts 107, 108, respectively. Each of the wheel mounts 107, 108 has a conical socket 109, 110 therein (FIG. 3) which is designed to receive the tapered ends 304, 305 of the axle 302 of the wheel assembly 300. The axle 302 can then be rotatably mounted within the wheel mounts 107, 108 by gently spreading the side walls 107, 108 and inserting the tapered ends of the axle 302 into the sockets 109, 100. The wheel mounts 107, 108 are preferably formed from plastic material, and they may be either integrally formed with the side walls or independently formed and fixed to the interior surfaces of the side walls by any suitable means, such as using adhesives.

In the embodiment shown in FIGS. 1 and 2, a ramp 400 is affixed to the bottom 105 of the container 100. This ramp 400 extends upwardly from the bottom 105 at an angle A (FIG. 2) sufficient to allow the ramp to rise above the circumference of the wheel assembly 300 when the wheel assembly 300 is mounted in the wheel mounts 107, 108. The upper surface 401 of the ramp is planar and is preferably provided with texturing so that it is not smooth. For example, the surface may be abraded, roughened, or knurled. This texturing of the surface 401 of the ramp 400 allows for better traction as insects ascend the ramp.

The ramp 400, like the other components of the insect amusement assembly 110, is preferably made from a suitable plastic material, is adhesively adhered to the bottom 105 of the container, and is spaced (as shown in FIGS. 1 and 2) from the end wall 103. The ramp is also of a small enough width that it is spaced from the side walls 101, 102 as well (FIG. 3).

The operation of the insect amusement assembly 10 is as follows. The cover 200 is removed from the container 100 and one or more insects, such as cockroaches, beetles, ants, caterpillars or any other of the myriad types of bugs, is placed into the container 100 through the open top 106. Once the insect is inside the container 100, the cover 200 is positioned within the side walls 101, 102 and the end walls 103, 104 until the curved surface 201 and end covers 202, 203 of the cover contact the side walls 101, 102 and end walls 103, 104, respectively. Inside the container, the insect or insects are free to roam about and crawl into the wheel assembly 300 by climbing onto the spokes 303 on the inside thereof. By being on the inside of the spokes 303 and walking forward, the wheel will rotate under the weight and movement of the insect as it climbs from spoke to spoke. In addition to being able to climb into the wheel, the insects may also walk up the ramp 400 on the roughened or textured surface 401 to the top of the wheel assembly 300, and by stepping off of the ramp 400 onto the outer edges of the spokes 303, the weight of the insect will cause the wheel assembly 300 to rotate and cause the insect to ride downward on the outside of the spokes 303.

Because the insect amusement assembly 10 is intended for use with only very small creatures such as bugs and insects, the overall dimensions of the container and cover are preferably no longer than five inches in length, one and one-half inches in width and one and one-half inches in height, when the cover 200 is in position in the open top 106 of the container 100. Furthermore, the wheel 301 preferably has a diameter of approximately no greater than one and one-half inches (preferably one and one-quarter inches) and the spokes 303 extending from the circular plate 301 are approximately one-quarter inch long, have a diameter of one-sixteenth of an inch and are spaced approximately one-sixteenth of an inch apart.

Without further elaboration, the foregoing will so fully illustrate my invention that others may, by applying current or future knowledge, readily adopt the same for use under various conditions of services.

What is claimed as the invention is:

1. An amusement device adopted to receive at least one insect therein, said device comprising:
    container means for receiving and containing said insect, said container means having an opening therein;
    cover means removably fitted into said opening in said container means for closing said opening;
    a wheel asssembly vertically mounted within said container means and rotatable about a horizontal axis; and
    a stepless ramp within said container means, said ramp being directed toward and extending over and above said wheel assembly, whereby an insect stepping off the end of said ramp steps onto said wheel assembly.

2. An amusement device as claimed in claim 1, wherein:
    said container means is comprised of a rectangular box, said box being open on one side thereof; and
    said cover means is comprised of: a curved outer surface, end pieces affixed to each end of said curved outer surface, and extensions fitted to and extending downward from the inside of said curved outer surface and said end pieces, said extensions being sized to fit within said open side of said container means.

3. An amusement device as claimed in claim 1, wherein said container means further comprises wheel mounting means for rotatably mounting said wheel assembly within said container means.

4. An amusement device as claimed in claim 3, wherein said wheel assembly is comprised of:
an axle receivable within said wheel mounting means;
a single circular plate axially mounted on said axle; and
a plurality of spokes parallel to said axle mounted around the circumference of said circular plate and extending away from said plate.

5. An amusement device as claimed in claim 4, wherein said stepless ramp is attached to the bottom of said container and extends upward at an incline over said spokes extending from said circular plate.

6. An amusement device as claimed in claim 5, wherein said ramp has a textured upper surface.

7. An amusement device as claimed in claim 1, wherein said container means and cover means are comprised of transparent material.

8. An amusement device as claimed in claim 1, wherein the lower end of stepless ramp contacts the bottom of said container means to permit said insect to mount said ramp.

* * * * *